United States Patent [19]

Raninger

[11] Patent Number: 4,478,999

[45] Date of Patent: Oct. 23, 1984

[54] PROCESS FOR THE PREPARATION OF PHENYLPYRIDAZINE COMPOUNDS

[75] Inventor: Franz Raninger, St. Florian, Austria

[73] Assignee: Chemie Linz Aktiengesellschaft, Linz, Austria

[21] Appl. No.: 484,553

[22] Filed: Apr. 13, 1983

[30] Foreign Application Priority Data

May 19, 1982 [DE] Fed. Rep. of Germany ....... 3218976

[51] Int. Cl.$^3$ .................... C07D 237/12; A01N 43/58
[52] U.S. Cl. .................................... 544/241; 424/250; 71/92
[58] Field of Search ......................... 544/241; 424/250

[56] References Cited

U.S. PATENT DOCUMENTS 3,953,445  4/1976  Schonbeck et al. ................ 544/241

Primary Examiner—Nicholas S. Rizzo
Attorney, Agent, or Firm—Wenderoth, Lind & Ponack

[57] ABSTRACT

A process for the preparation of O-[3-phenyl-6-chloro-4-pyridazinyl] S-(alkyl) thiocarbonates by reaction of alkali metal salts of 3-phenyl-4-hydroxy-6-chloropyridazine with alkyl thiochloroformates in a water/acetone solution.

4 Claims, No Drawings

PROCESS FOR THE PREPARATION OF PHENYLPYRIDAZINE COMPOUNDS

The invention relates to a process for the preparation of phenylpyridazine compounds in a water/acetone medium.

It has been disclosed in U.S. Pat. No. 3,953,445 that 3-phenyl-6-chloropyridazine thiocarbonates have valuable herbicidal properties. Likewise, their preparation by reaction of the compound 3-phenyl-4-hydroxy-6-chloropyridazine or its salts with alkyl thiochloroformates is described in this citation, the reaction optionally taking place with the addition of an acid acceptor, namely a tertiary amine. It is possible dispense with the addition of the acid acceptor, primarily when the 3-phenyl-4-hydroxy-6-chloropyridazine is employed in the form of its salt with tertiary amines. The reaction is preferably carried out in the presence of inert solvents, such as aromatic hydrocarbons, while, on the other hand, it is recommended that care should be taken that compounds containing hydroxyl groups, such as alcohols or water, should be absent.

In practice, this process does not meet all requirements, since the tertiary amines acting as acid acceptors, irrespective of whether they have been employed as such or in the form of salts with the pyridazine compound, are converted during the reaction into hydrochlorides which must either be discarded, involving a heavy effluent load, or worked up in a separate process, which imposes a severe economic strain on the overall process. Furthermore, it has been found that small amounts of tertiary amines, particularly in the presence of water, act to decompose compounds of the formula I (below). In addition, the inert aromatic hydrocarbons, which are mentioned as the reaction medium and which are difficult to remove completely from the active compound, exhibit even in residual amounts an undesirable plant toxicity and should for this reason be avoided. Finally, since it is necessary to start with dried, anhydrous compounds, water must be avoided. This is a disadvantage because the 3-phenyl-4-hydroxy-6-chloropyridazine contains water as a result of the method of preparation.

Surprisingly, it has now been found that the preparation of the compounds of the formula I can be carried out very readily in the presence of water when it is carried out in a water/acetone solvent system. By this means, it is possible to dispense with the costly drying of 3-phenyl-4-hydroxy-6-chloropyridazine which is otherwise necessary. The use of the alkali metal salts as starting material has not hitherto been considered because they crystallize with 2 moles of water of crystallization which are very difficult to remove completely by drying.

Accordingly, the present invention relates to a process for the preparation of phenylpyridazine compounds of the general formula

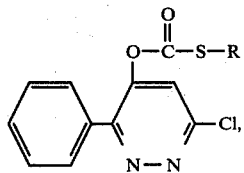   I wherein R is a straight-chain or branched alkyl radical having 1 to 18 C atoms, which comprises reacting alkali metal salts of 3-phenyl-4-hydroxy-6-chloropyridazine with alkyl thioformates of the formula

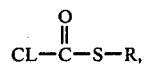   II wherein R is defined as in formula I, in a water/acetone solution at a temperature from 5° to 60° C., separating off the aqueous phase formed, which contains the alkali metal chloride and which has a higher specific gravity, and obtaining the pure phenylpyridazine compound of the formula I by evaporating the acetone from the remaining acetone solution.

The parent compound 3-phenyl-4-hydroxy-6-chloropyridazine is obtained in a known manner by heating 3-phenyl-4,6-dichloropyridazine with sodium hydroxide solution and subsequent acidification and removal by centrifugation. It has proved to be particularly advantageous not to dry the parent compound but to suspend it, in the state still moist from the centrifuge, in a mixture of acetone and water and to add aqueous alkali metal hydroxide of a known concentration until a clear solution has been produced and the theoretical amount of alkali has been consumed. This occurs at a pH of about 8.8 to 9.7. By this means, the exact concentration of the parent compound is known without it being previously dried and weighed, and the amount of alkyl thiochloroformate necessary for the reaction can easily be worked out from the amount of alkali consumed. In particular, aqueous sodium hydroxide or potassium hydroxide can serve as the alkali metal hydroxide.

The parent compound can be suspended in water and then acetone added, or it can be suspended in acetone and then water added, or it can be suspended in a mixture of acetone and water. It is preferred that the mixture of acetone and water contains 50 to 75% by weight of acetone and 25 to 50% by weight of water. An acetone content of 60 to 70% by weight and a water content of 30 to 40% by weight is particularly preferred.

It is also possible to prepare the alkali metal salt of the parent compound separately and to dissolve it as such in the mixture of acetone and water, but the production of a solution of the alkali metal salt in situ is particularly preferred.

The calculated amount of alkyl thiochloroformate is added, as quickly as possible and with vigorous stirring, to the solution of the alkali metal salt of the parent compound. The reaction should be carried out at a temperature from 0° to 60° C., in particular at a temperature from 10° to 40° C., and since the reaction is slightly exothermic, if necessary, it can be cooled in order to remain within the desired temperature range. After a reaction time of about 1 to 2 hours, the stirrer is switched off, whereupon two phases are easily produced, without the formation of an intermediate layer: an organic phase of lower specific gravity, containing O-[3-phenyl-6-chloro-4-pyridazinyl]S-(alkyl) thiocarbonate and acetone, and a phase of higher specific gravity, containing water, alkali metal chloride and a little acetone. The aqueous phase is separated off and the acetone contained therein is distilled off and reused, so that the effluent produced is only an aqueous solution of sodium chloride or alkali metal chloride.

The acetone, together with the traces of water, is distilled out of the organic phase which only contains traces of water, and the phenylchloropyridazinyl alkyl thiocarbonate then remains in virtually 100% yield.

EXAMPLE 1

550 liters of acetone were initially introduced into a 1,500 liter stirred vessel and 300 kg of 3-phenyl-4-hydroxy-6-chloropyridazine, moist from the centrifuge, were added with stirring and then 220 liters of water were introduced. Subsequently, 51.0% strength sodium hydroxide solution was added until a pH of 9.5 was reached and a clear solution had been produced. 93.7 kg of sodium hydroxide solution was used. Then 254.6 kg of 98% pure octyl thiochloroformate were introduced at 30° C. over 4 to 5 minutes. The temperature rose to 35° C. within a few minutes. The reaction temperature was maintained between 35° to 37° C. by cooling. The pH fell to about 4.5 within one hour. Reaction was allowed to continue for a total of 2 hours, and then the stirrer was switched off, the mixture was allowed to stand for 30 minutes and the aqueous phase of higher specific gravity was separated off. The acetone was rapidly distilled out of the organic phase. 456 kg of technical product were obtained, corresponding to a yield of 99.6%.

EXAMPLE 2

A mixture of 550 ml of acetone, 320 ml of water and 300 g of moist 3-phenyl-4-hydroxy-6-chloropyridazine were suspended in a 2 liter four-neck flask and the pH was adjusted to 9.5 with a 44.7% strength aqueous solution of potassium hydroxide, with stirring. A clear solution formed and 174.4 g of potassium hydroxide solution were used. The solution was cooled down to 25° C. and 295 g of n-octyl thiochloroformate (98% pure) was added, with vigorous stirring, within 1 minute. The temperature rose to 40° C. over 15 minutes and then decreased again to 31° C. in the next 105 minutes.

The stirrer was switched off and, after a settling time of 10 minutes, the layers were separated.

The organic phase was evaporated in a rotary evaporator and the residual acetone was removed in vacuo at 80° C. 536 g of oily product were obtained. Yield=99.2%.

EXAMPLE 3

935 ml of acetone, 374 ml of water and 350 g of 3-phenyl-4-hydroxy-6-chloropyridazine, moist from the centrifuge, were suspended in a 2 liter three-neck flask and the pH was adjusted to 9.5 with 144 g of 48.1% strength NaOH.

222 g of ethyl thiochloroformate were added at 25° C. over 2 minutes. The temperature rose to 39° C. in the course of 10 minutes. Reaction was allowed to continue for a total of 2 hours, and then the stirrer was switched off and the phases were separated. The solvent was completely distilled off, in vacuo in a rotary evaporator, from the organic phase of a lower specific gravity, and 511 g of oily O-[3-phenyl-6-chloro-4-pyridazinyl]S-ethyl thiocarbonate were obtained. Yield 100%.

EXAMPLE 4

200 ml of acetone, 100 ml of water and 100 g of 3-phenyl-4-hydroxy-6-chloropyridazine, moist from the centrifuge, were mixed in a 1 liter three-neck flask and the pH was adjusted to 9.6 with 39.4 g of 48.1% strength NaOH. The solution was cooled down to 25° C. and 67.0 g of 98% pure isopropyl thiochloroformate were added over 30 seconds.

After 4 minutes, the temperature had reached 40° C. and the pH had reached 7.5. The mixture was stirred for 2 hours, during which the pH decreased to 4.5. After switching off the stirrer, the layers were separated and the phase of higher specific gravity, containing NaCl, was separated off. The phase of lower specific gravity was freed of solvent in vacuo in a rotary evaporator and 146.0 g of oily O-[3-phenyl-6-chloro-4-pyridazinyl]S-isopropyl thiocarbonate were obtained. This corresponds to a 100% yield.

EXAMPLE 5

As described in Example 4, 100 g of 3-phenyl-4-hydroxy-6-chloropyridazine, moist from the centrifuge, were brought to pH 9.6 with 39.0 g of 48.1% strength NaOH and, at 25° C., 73 g of 98% pure isobutyl thiochloroformate were added and reaction was allowed to continue with stirring for 2 hours. The maximum reaction temperature reached was 40° C. and the pH reached was 4.2.

After phase separation and separation off of the aqueous phase, the solvent was evaporated from the organic phase of lower specific gravity. 151 g of O-[3-phenyl-6-chloro-4-pyridazinyl]S-isobutyl thiocarbonate was produced as an oily product, corresponding to a yield of 100%.

What we claim is:

1. A process for preparing a phenylpyridazine compound of the formula

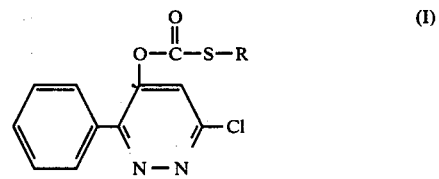

(I)

wherein R is straight-chain or branched alkyl having 2 to 8 carbon atoms, which comprises reacting an alkali metal salt of 3-phenyl-4-hydroxy-6-chloropyridazine with an alkyl thioformate of the formula

(II)

wherein R is as defined above, in a water/acetone solution containing 50 to 75% by weight of acetone and 25 to 50% by weight of water, at a temperature from 5° to 60° C., separating off the resultant aqueous phase, which contains alkali metal chloride and which has a higher specific gravity than the resultant organic phase, and recovering a substantially pure phenylpyridazine compound of the formula I by evaporating the acetone from the organic phase.

2. A process according to claim 1, in which the water/acetone solution contains 60 to 70% by weight of acetone and 30 to 40% by weight of water.

3. A process according to claim 1, in which the reaction is carried out at a temperature of 10° to 40° C.

4. A process according to claim 1, in which the alkali metal salt is formed in situ from 3-phenyl-4-hydroxy-6-chloropyridazine and an aqueous solution of alkali metal hydroxide of known concentration.

* * * * *